United States Patent [19]

Smalley et al.

[11] Patent Number: 4,939,922
[45] Date of Patent: Jul. 10, 1990

[54] METHOD AND DEVICE FOR EXAMINING THE WEAR AND FRICTION PROPERTIES OF SURFACE MATERIALS EXPOSED TO SLIDING FRICTION

[75] Inventors: Robert J. Smalley, Leerdam; Maarten Noordman, Hilversum, both of Netherlands

[73] Assignee: SKF Industrial Trading and Development Co. B.V., Nieuwegein, Netherlands

[21] Appl. No.: 203,232

[22] Filed: Jun. 6, 1988

[30] Foreign Application Priority Data

Jul. 2, 1987 [NL] Netherlands ................. 8701557

[51] Int. Cl.$^5$ ............................................. G01N 19/02
[52] U.S. Cl. ............................................. 73/10; 73/9; 374/51
[58] Field of Search ............... 73/10, 9, 7; 374/46, 374/47, 51

[56] References Cited

U.S. PATENT DOCUMENTS

| 2,020,565 | 11/1935 | Neely et al. | 73/10 |
|---|---|---|---|
| 2,909,056 | 10/1959 | Neely | 73/10 |
| 3,045,471 | 2/1962 | Chapman et al. | 73/10 |
| 3,166,927 | 1/1965 | Sonntag et al. | 73/10 |
| 3,353,398 | 11/1967 | Lohmar et al. | 73/10 |
| 3,602,035 | 8/1971 | Spohn et al. | 73/10 |
| 3,785,196 | 1/1974 | Smith | 73/10 X |
| 3,913,377 | 10/1975 | Lindeman | 73/10 |
| 3,972,221 | 8/1976 | Natens et al. | 73/9 |
| 4,095,461 | 6/1978 | Storita | 73/815 |
| 4,712,418 | 12/1987 | Augustin | 73/10 X |

FOREIGN PATENT DOCUMENTS

| 2853128 | 6/1979 | Fed. Rep. of Germany | 73/10 |
|---|---|---|---|
| 2277342 | 1/1976 | France | 73/10 |
| 161136 | 3/1964 | U.S.S.R. | 73/10 |
| 193780 | 5/1967 | U.S.S.R. | 73/10 |
| 232595 | 4/1969 | U.S.S.R. | 73/10 |
| 645060 | 1/1979 | U.S.S.R. | 73/10 |

OTHER PUBLICATIONS

"Energy Input Held Constant in New Friction Material Testing Machine"; *Automotive Industries;* Jun. 15, 1935; pp. 802,808; by Edward P. Culver et al; in 73/9.

*Primary Examiner*—Tom Noland
*Attorney, Agent, or Firm*—Rosen, Dainow & Jacobs

[57] ABSTRACT

Method for examining the sliding friction between exposed surfaces of different combinations of materials, characterized by the fact that a first test piece of a first type of material and a second test piece of a second type of material are moved against one another over a certain distance and under a certain load while a lubricant is applied between the exposed surfaces, whereby the required energy is measured and this step is subsequently repeated a number of times at various bulk temperatures of the lubricant, following which the measured energy consumption is plotted on a graph as a function of the bulk temperature of the lubricant.

9 Claims, 5 Drawing Sheets

METHOD AND DEVICE FOR EXAMINING THE WEAR AND FRICTION PROPERTIES OF SURFACE MATERIALS EXPOSED TO SLIDING FRICTION

BACKGROUND OF THE INVENTION

The invention concerns a method and a device for examining the wear and friction properties of surface materials exposed to sliding friction.

Thus far, for the study of the wear and friction properties of surface materials one has to rely on practical tests whereby the components for which the materials are ultimately destined are incorporated in the machine in question. For example, when checking the valve plates operating in conjunction with the lobes of a camshaft in car engines, the engines are tested on the test bench or the cars are tested on the test track in order to check the action of the valve plates. Similar tests require a lot of time and money before yielding data offering reliable predictions about the properties of the components or the materials.

The invention aims at providing a method which effectively overcomes the aforementioned drawbacks while offering a fast and simple way of predicting the wear and/or friction properties of materials.

SUMMARY OF THE INVENTION

For this purpose, the method according to the invention is characterized by the fact that a first test piece of a first type of material and a second test piece of a second type of material are moved against one another over a certain distance and under a certain load while a lubricant is applied between the exposed surfaces, whereby the required energy is measured and this step is subsequently repeated a number of times at various bulk temperatures of the lubricant, following which the measured energy consumption is plotted on a graph as a function of the bulk temperature of the lubricant.

A surprise discovery was made in the sense that this fast and cheap method provides excellent insight into the wear and friction behavior of surface materials. Depending on the load and the variable temperature, various lubrication conditions will occur between the two test surfaces. A constant load cycle will yield—at a low bulk temperature of the lubricant and thus a high degree of viscosity of the latter—a full-film lubrication between the test surfaces. When the temperature is raised and, consequently, the viscosity of the lubricant is lowered, the bearing capacity of the lubricant film will undergo a transition from full-film lubrication to mixed lubrication, followed by border lubrication. If the energy needed for a certain displacement between both test pieces is plotted on a graph as a function of the bulk temperature of the lubricant, the transitions between the aforementioned types of lubrication are easy to recognize. The lower the temperature at which a transition occurs—and the lower the energy use for a certain temperature (low friction coefficient)—the better the wear and friction properties will be for a combination of surface materials. It is obvious that the energy use for full-film lubrication will yield better information about the surface layers of the material, while the energy use for border lubrication will provide above all indications about border layers of the material formed with additives from the lubricant.

If the tests are continued over long periods of time it is also possible to examine the wear and tear profiles of the exposed surfaces.

In a specific form of execution of the method according to the invention, both test pieces are moved alongside one another under changing loads whereby preferably the first piece is driven by rotation while the second piece is moved against the first piece by spring action. As the first test piece, a cam or eccentric ring may be used.

This procedure provides a simple way for simulating a condition of sliding friction between a camshaft lobe and a valve plate in a combustion engine. Thus it is possible, with very simple means, to gain insight into the behavior of the surface material of the valve plate, which means that this test provides a basis for a well-founded selection of materials.

To measure the energy dissipated by friction between the test piece surfaces, one can measure the torque at the driven axle of the first test piece. Another possibility, of course, is to measure the force on the second test piece in the direction of the displacement of the first test piece over the second test piece. From the torque measured and the angle traversed, or from the transverse force measured and the friction path covered, it is possible by means of simple numerical calculations to calculate the energy consumption per revolution of the cam or eccentric ring.

As mentioned earlier, the invention also concerns a device for examining the wear and friction properties of surface materials exposed to sliding friction.

According to the invention this device is characterized by a holder for a first test piece of a first material, a holder for a second test piece of a second material, driving means for moving the first and second test pieces with respect to one another, means for loading the first and second test pieces with respect to one another, means for measuring the energy needed for the relative displacement between the first and the second test pieces, means for supplying a lubricant to the exposed surfaces of the first and second test pieces, and means for heating the lubricant and keeping it at a certain temperature.

BRIEF DESCRIPTION OF THE DRAWING

The invention shall be explained hereafter with the aid of the drawing which provides an example of an execution of the invention.

DETAILED DESCRIPTION

Figure 1:
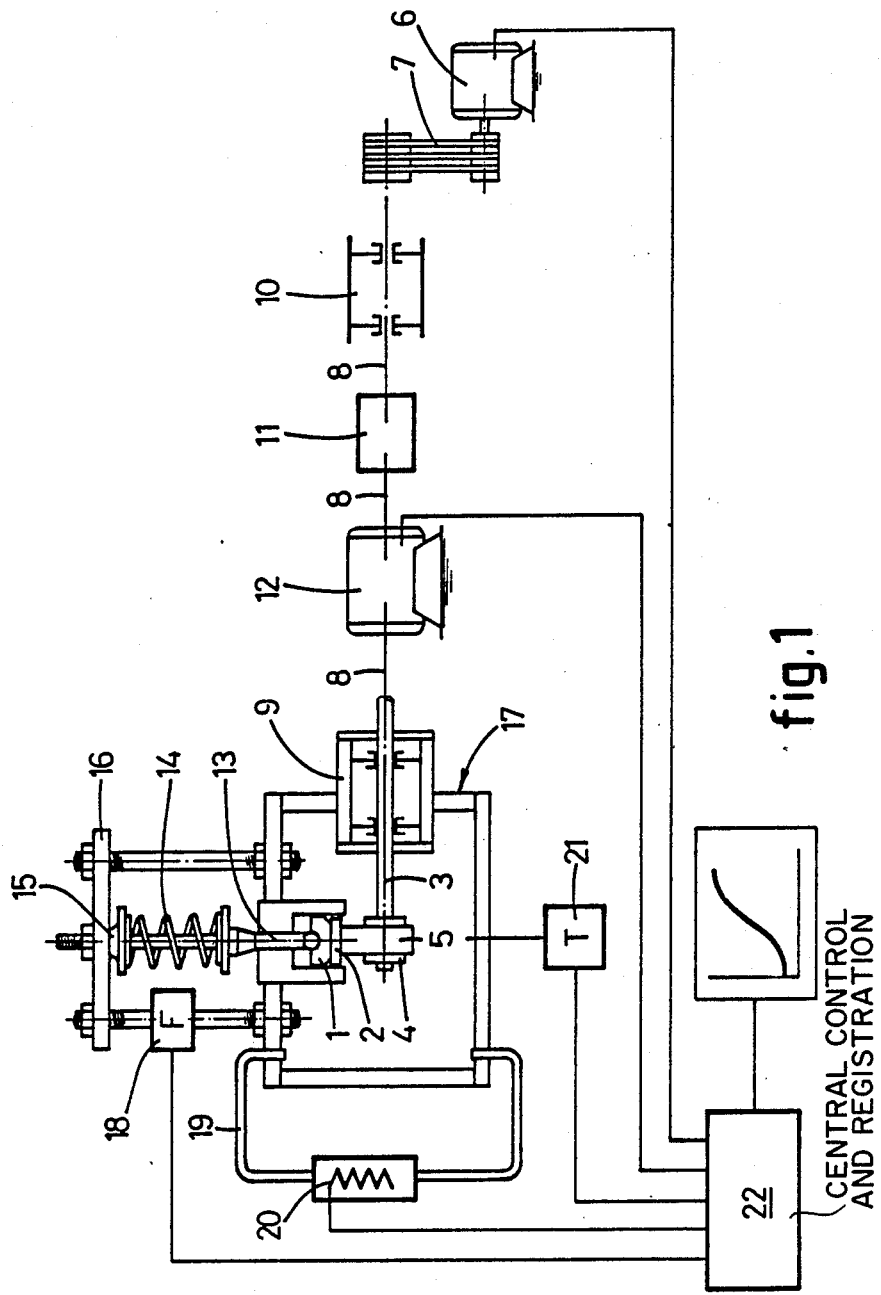
FIG. 1 is a schematic rendering of one execution of the device according to the invention for examining the wear and friction properties of surface materials exposed to sliding friction.

FIG. 1 shows in a highly schematic fashion the device for examining the wear and friction properties of surface materials. The device serves in particular for testing valve plates for combustion engines. The device has a holder 1 for a first test piece in the form of a disc 2, and a holder 4 mounted on a horizontal axle 3 for holding a second test piece in the form of an eccentric ring 5. The axle 3 can be driven in a rotating fashion by means of an electric motor 6 which by means of a belt transmission 7 grasps the axle train 8 containing the axle 3. The axle train is carried by two rigid bearing units 9 and 10. In addition, between the bearing units 9 and 10, the axle train 8 holds a vibration damper 11 and a torque recorder 12. The torque recorder 12 serves to measure the moment on the axle train 8 resulting from the sliding friction between the eccentric ring and the disc. The holder 1 for holding the disc 2 is caught by a more or less vertical rod 13 which can glide back and forth and is tensioned by a spiral spring 14, so that the disc 2 is loaded by spring pressure against the eccentric ring 5.

By way of a guide 15 before the rod 13, the spiral spring 14 rests against a seat 16 mounted on a housing 17. Between the seat 16 and the housing 17 a force recorder 18 has been installed for measuring the force exerted by the spring 14 on the rod and therefore of the force exerted by the disc 2 on the eccentric ring 5.

The inner space of the housing 17 contains the holders 1 and 4 for both test pieces, or the disc 2 and the eccentric ring 5, and this inner space can be filled with a lubricant for lubricating both test pieces 2 and 5. The housing is connected to a lubricant circuit 19 which includes a heating element 20. This heating element 20 is controlled by means of a temperature recorder 21 which measures the bulk temperature of the lubricant in the housing 17.

The motor 6, the torque recorder 12, the force recorder 18, the heating element 20 and the temperature recorder 21 are connected to a central control and registration unit 22.

Figure 2:
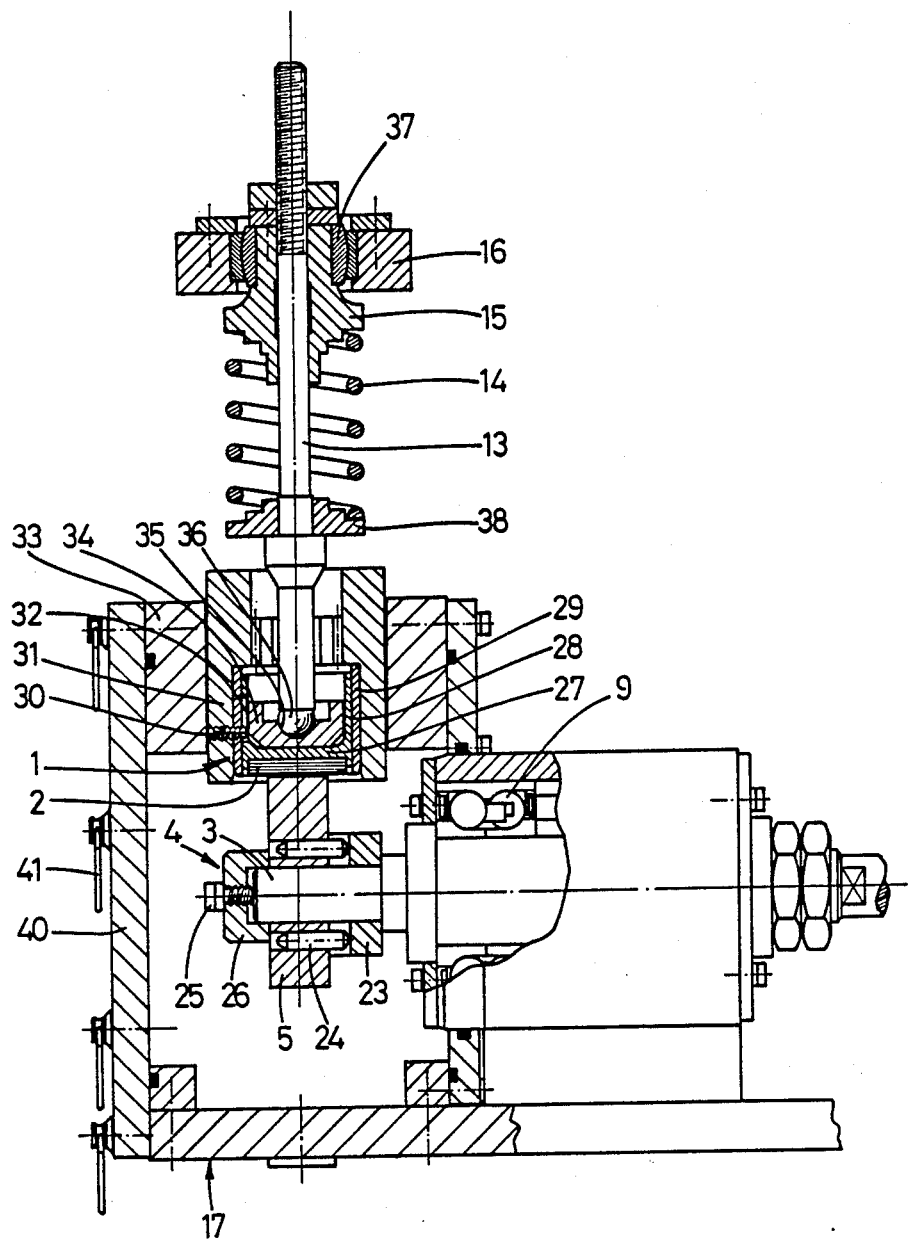
FIG. 2 is a vertical cross-section of one part of the device according to FIG. 1.
Figure 3:
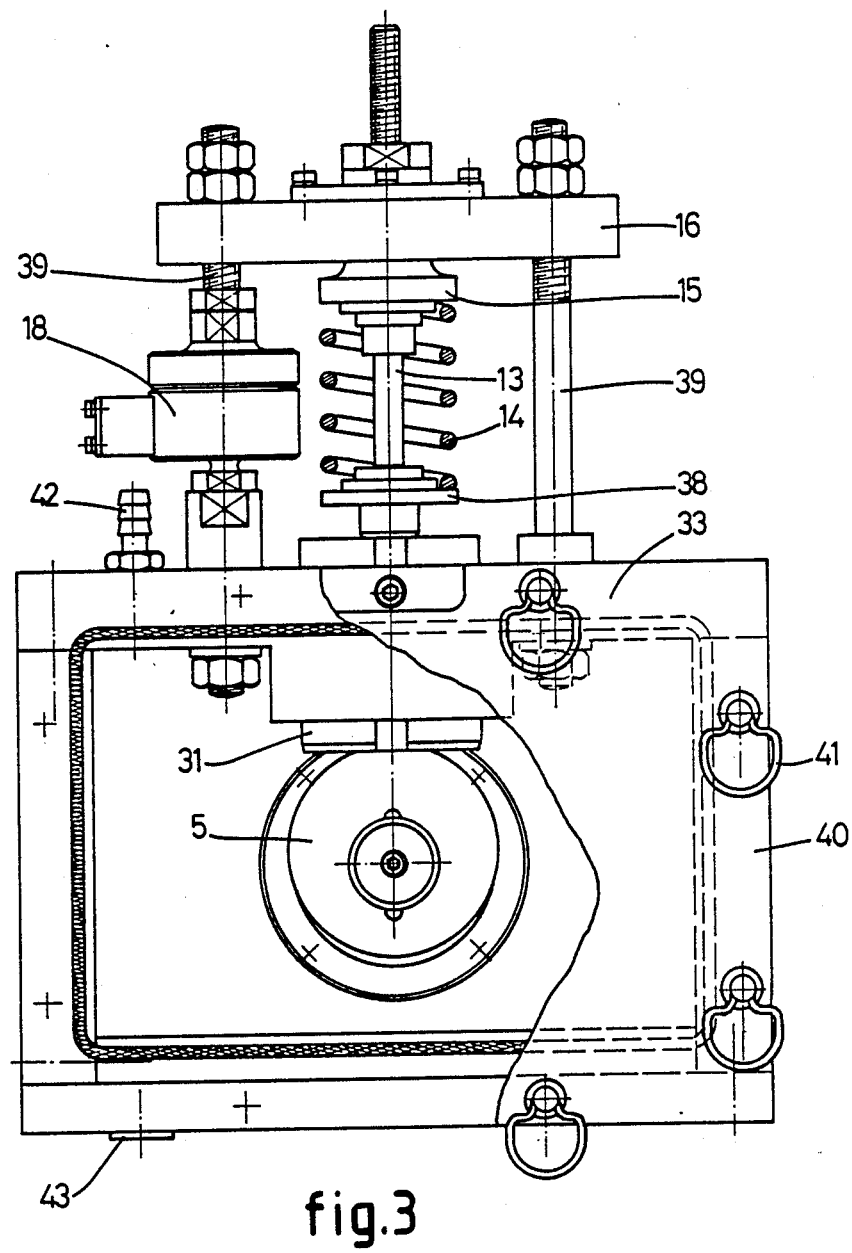
FIG. 3 is a front view, partially in cross-section, of the device according to FIG. 2.

In FIGS. 2 and 3, the device for examining the friction between the exposed surfaces is rendered in greater detail. It shows that the holder 4 for holding the eccentric ring 5 on the axle 3 consists of locking pins 24 inserted in the eccentric ring 5 and in a locking element 23, and a pressure element 26 which can be fastened by means of a screw 25 and serves to press the eccentric ring 5 against the locking element 23.

The holder 1 for the disc 2 consists of a bowl-shaped element and the disc 2 is pressed into the bottom 27 of this bowl-shaped element, while the cylindrical wall 28 can slide into a sleeve 29 which by means of a locking screw 30 is fastened in a casing 31. The locking screw 30 also prevents the holder 1 from being twisted inside the sleeve 29 because the locking screw 30 protrudes into a longitudinal slot 32 in the cylindrical wall 28 of the holder 1. The casing 31 is mounted in a thicker section of the upper wall 33 of the housing 17.

Within the cylindrical wall 28 of the holder 1 a dish 34 has been installed with a spherical depression 35. The rod 13 impacts the holder 1 by means of a ball 36 located between the lower extremity of the rod 13 and the depression 35 in the dish 34.

Near its upper extremity the rod 13 can slide inside the guide 15 which is carried in the seat 16 by means of a spherical bearing 37. The spiral spring 14 is locked in between this guide 15 and a spring retainer 38 resting on a shoulder of the rod 13. The spiral spring 14 constantly presses the rod 13 downward so that the disc 2 is pushed against the eccentric ring 5. Because of the spherical bearing 37 and the ball support, the rod 13 is capable of exerting pure pressure on the disc 2, without any bending moment.

The force recorder 18 is contained in one of the tap bolts 39 for supporting the seat 16 on the housing 17. By means of this force recorder 18 and the torque recorder 12 the momentary friction coefficient between the disc 2 and the eccentric ring 5 can be calculated.

A front wall 40 of the housing 17 is made of a transparent material and can be removed by simply loosening the snap locks 41. The connections 42 and 43 of the housing are intended for connecting the lines of the lubrication circulation system 19.

The method according to the device is as follows.

The axle 3 and therefore the eccentric ring 5 are driven by means of the electric motor 6 with a given number of revolutions. The eccentric ring 5 rotates against the disc 2 whereby the spiral spring 14 places a load on the disc 2 so that the disc 2 follows the eccentric motion of the eccentric ring 5. The lubricant in the housing 17 is kept at a constant temperature by means of the control unit 22. The torque recorder 12 measures the counter-moment exerted by the friction between the disc 2 and the eccentric ring 5 on the axle 3. From the constantly measured moment the energy expended by the friction between the disc 2 and the eccentric ring 5 can be calculated numerically via the integral over one revolution of the moment dependent on the angle. The energy use is recorded over one revolution together with the accompanying bulk temperature of the lubricant by the control and recording unit 22. Similar measurements are repeated a number of times whereby the bulk temperature is raised every time.

Figure 4:
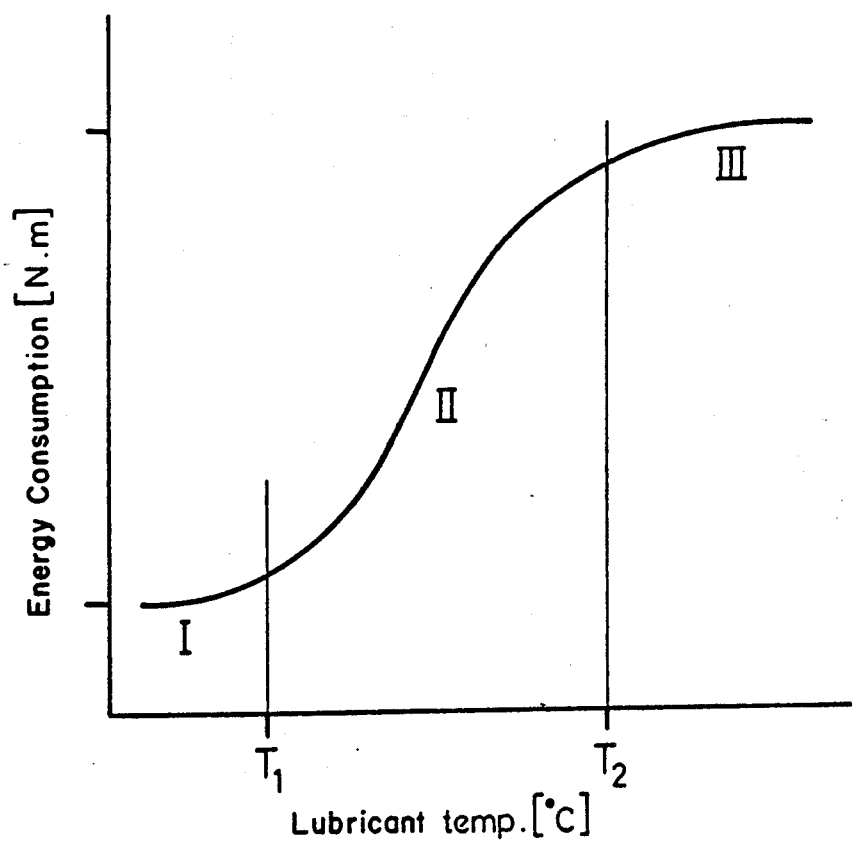
FIG. 4 shows a graph representing the theoretical curve of the energy consumption as a function of the lubricant temperature.

FIG. 4 shows a graph in which the vertical coordinate represents the energy use per revolution of the eccentric ring and the horizontal coordinate represents the bulk temperature of the lubricant. The energy use as a function of the lubricant temperature is characteristic to the point that a number of properties of the combination of materials regarding sliding friction and wear and tear can be derived from it.

First, three temperature zones I, II and III can be distinguished, indicating specific lubrication conditions. The first zone I, extending all the way to a transition temperature $T_1$, indicates the presence of a full-film lubrication between the disc 2 and the eccentric ring 5. Here the energy use is low. An increase in the temperature of the lubricant leads to a large increase in energy consumption after the transition temperature $T_1$ in the zone II, which can be explained by the appearance of mixed lubrication between the disc 2 and the eccentric ring 5, whereby any rough high spots on both exposed surfaces are in contact with one another. As the temperature of the lubricant increases—and the viscosity of the lubricant decreases and therefore also the bearing capacity of the lubricant film—the contact between the rough high spots grows steadily, leading to an increase in friction between the two elements and thus in energy use.

At a transition temperature $T_2$, the condition of mixed lubrication turns into a condition of border lubrication (zone III), whereby the energy use no longer increases when the temperature of the lubricant is raised. It is even possible that the energy use will drop because at a certain temperature the additives of the lubricant start adhering to the metal surface of the disc 2 and/or the eccentric ring 5, and start acting as border lubricant.

Figure 5:
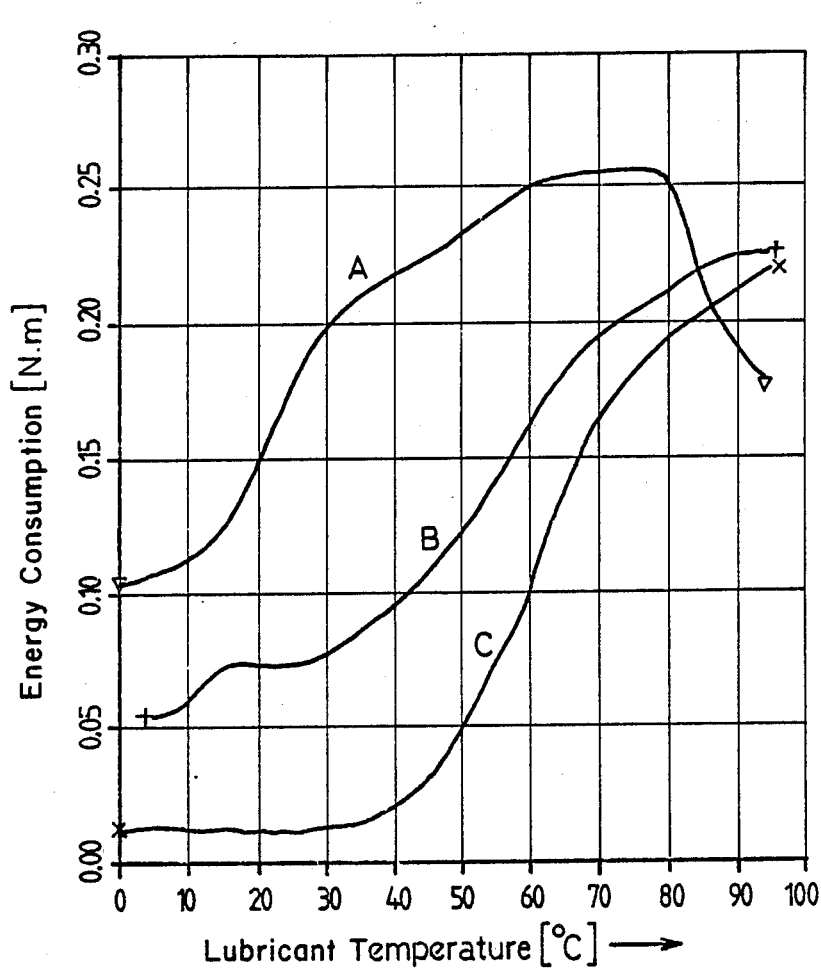
FIG. 5 shows the same graph as FIG. 4 but the curve of the energy consumption is presented for three different combinations of materials.

It should be obvious that a material possesses favorable friction properties if the energy use is low and the transition temperatures $T_1$ and $T_2$ are high. FIG. 5 shows three curves, A, B and C, with curve A belonging to a test piece 2 of 52100 steel with surface cementing. Curve B representing a test piece 2 of DIN 17220 steel with surface cementing, while curve C represents the results for a test piece 2 DIN 17220 steel which has undergone vacuum heat treatment.

All these cases make use of an eccentric circle 5 made of a ball bearing steel known by the name of SKF 3, while standard motor oil is used as the lubricant.

It appears clearly from the graph in FIG. 5 that the combination of the eccentric ring 5 of SKF 3 steel and the disc 2 of DIN 17220 steel with vacuum heat treatment possesses the most favorable properties with regard to sliding friction. A comparison between wear and tear profiles of the different test discs 2 indicates furthermore that this combination is also the most favorable with regard to wear and tear.

According to the invention a method and a device for examining the wear and friction properties of surface materials exposed to sliding friction have been created which are very simple, which provide fast insight into the behavior of materials, and which yield reliable results.

The invention is not limited to the model of execution described above and shown in the drawing, which model can be varied in several ways within the framework of the invention.

We claim:

1. Device for examining the sliding friction between exposed surfaces for different combinations of materials, characterized by a holder for a first test piece of a first material, a holder for a second test piece of a second material, driving means for moving the first and second pieces with regard to one another, means for loading the first and second test pieces with regard to one another, means for measuring the energy needed for the relative displacement between the first and the second test pieces, means for supplying a lubricant to the exposed surfaces of the first and second test pieces, and means for heating the lubricant and keeping it at a certain temperature.

2. Device according to claim 1, characterized by the fact that the holder of the first test piece has been mounted on an axle which can be driven in a rotating fashion, while the holder of the second test piece is tensioned, loaded by spring action and capable of sliding back and forth.

3. Device according to claim 2, characterized by the fact that the first test piece consists of a cam means and the second test piece of a test plate held perpendicular to the first test piece.

4. Device according to claims 2 or 3, characterized by the fact that the rotating axle of the first test piece contains a torque meter.

5. Device according to claim 2, characterized by the fact that the holder of the second test piece is grasped by a substantially vertical rod which is tensioned by means of a spring element while on the one hand the rod rests by means of a ball-retaining support against the holder, and on the other hand it is guided to slide in a guide suspended by a spherical bearing.

6. Device according to one of the claims 1 through 3 or 5, characterized by the fact that the holder of the first test piece and the holder of the second test piece are contained inside a housing which serves as a reservoir for the lubricant.

7. Device according to claim 2, characterized by the fact that the first test piece consists of an eccentric disc and the second test piece of a test plate held perpendicular to the first test piece.

8. Device for examining the sliding friction between exposed surfaces for different combinations of materials, characterized by a first holding means for a first test piece of a first material, a second holding means for a second test piece of a second material, driving means for moving the first and second pieces with regard to one another, means for loading the first and second test pieces with regard to one another, means for measuring the energy needed for the relative displacement between the first and the second test pieces, means for supplying a lubricant to the exposed surfaces of the first and second test pieces, and means for heating the lubricant and keeping it at a certain temperature, the first test piece comprising an eccentric means, said second holding means for holding the second test piece movably against the first test piece and said second holding means holding said second test piece against an edge of the first test piece.

9. Device according to claim 8, wherein said first holding means holds the first test piece without any bending moment thereon.

* * * * *

UNITED STATES PATENT AND TRADEMARK OFFICE
CERTIFICATE OF CORRECTION

PATENT NO. : 4,939,922

DATED : July 10, 1990

INVENTOR(S) : Robert J. Smalley, Maarten Noordman

It is certified that error appears in the above-identified patent and that said Letters Patent is hereby corrected as shown below:

Column 5, line 5, after "piece 2" insert --of--.

Signed and Sealed this

Second Day of March, 1993

*Attest:*

STEPHEN G. KUNIN

*Attesting Officer*     *Acting Commissioner of Patents and Trademarks*